US011839403B2

(12) United States Patent
Fojtik

(10) Patent No.: US 11,839,403 B2
(45) Date of Patent: Dec. 12, 2023

(54) TISSUE PIERCING ASSEMBLIES

(71) Applicant: Distal Access, LLC, Park City, UT (US)

(72) Inventor: Shawn P. Fojtik, Park City, UT (US)

(73) Assignee: Distal Access, LLC, Park City, UT (US)

(*) Notice: Subject to any disclaimer, the term of this patent is extended or adjusted under 35 U.S.C. 154(b) by 562 days.

(21) Appl. No.: 15/890,310

(22) Filed: Feb. 6, 2018

(65) Prior Publication Data

US 2018/0228509 A1    Aug. 16, 2018

Related U.S. Application Data

(60) Provisional application No. 62/455,588, filed on Feb. 6, 2017.

(51) Int. Cl.
*A61B 17/34* (2006.01)
*A61B 10/02* (2006.01)
*A61B 17/00* (2006.01)

(52) U.S. Cl.
CPC ........ *A61B 17/3415* (2013.01); *A61B 10/025* (2013.01); *A61B 10/0233* (2013.01);
(Continued)

(58) Field of Classification Search
CPC ............ A61B 17/3415; A61B 10/0233; A61B 17/3472; A61B 17/3423; A61B 10/025;
(Continued)

(56) References Cited

U.S. PATENT DOCUMENTS 5,197,484 A     3/1993  Kornberg et al.
6,312,394 B1 *  11/2001 Fleming, III ........ A61B 10/025
                                                   600/567
(Continued)

FOREIGN PATENT DOCUMENTS

EP     0974305 A2    1/2000
EP     2197367 A1    6/2010
(Continued)

OTHER PUBLICATIONS

USPTO as International Searching Authority, "International Search Report and Written Opinion," International application No. PCT/US2018/017133, dated May 14, 2018.
(Continued)

*Primary Examiner* — Patrick Fernandes
*Assistant Examiner* — Joseph A Tombers
(74) *Attorney, Agent, or Firm* — DENTONS Durham Jones Pinegar

(57) ABSTRACT

A cannula-stylet assembly for piercing tissues of a subject's body includes a stylet that is significantly longer than the cannula. The length of the stylet enables introduction of the stylet through the length of both the cannula and a gripping device that has been coupled to a proximal end of the cannula. A medical piercing system may include a cannula-stylet assembly with a long stylet and a gripping device that may remain assembled with the cannula when the stylet is removed from the cannula or a gripping device that remains assembled with a stylet of a conventionally configured cannula-stylet assembly when the stylet is removed from the cannula.

23 Claims, 5 Drawing Sheets

(52) U.S. Cl.
CPC ...... *A61B 17/3423* (2013.01); *A61B 17/3472* (2013.01); *A61B 10/0283* (2013.01); *A61B 17/3417* (2013.01); *A61B 2010/0208* (2013.01); *A61B 2017/00367* (2013.01); *A61B 2017/00407* (2013.01); *A61B 2017/00473* (2013.01); *A61B 2017/00477* (2013.01); *A61B 2017/3409* (2013.01)

(58) Field of Classification Search
CPC .. A61B 2017/00407; A61B 2017/3409; A61B 17/3417; A61B 10/0283; A61B 2017/00367; A61B 2017/00477; A61B 2017/00473; A61B 2010/0208
See application file for complete search history.

(56) References Cited

U.S. PATENT DOCUMENTS

| | | |
|---|---|---|
| 7,179,232 B2 | 2/2007 | Sutton et al. |
| 7,278,970 B2 | 10/2007 | Goldenberg |
| 8,845,621 B2 | 9/2014 | Fojtik |
| 9,107,691 B2 | 8/2015 | Fojtik |
| 10,352,411 B2 | 7/2019 | Fojtik |
| 2004/0073139 A1* | 4/2004 | Hirsch ................ A61B 10/025 600/564 |
| 2004/0127814 A1* | 7/2004 | Negroni ............... A61B 10/025 600/567 |
| 2007/0255282 A1 | 11/2007 | Simonton et al. |
| 2008/0208075 A1 | 8/2008 | Goldenberg |
| 2009/0270862 A1 | 10/2009 | Arcenio |
| 2012/0239008 A1* | 9/2012 | Fojtik ................... A61M 25/01 606/1 |
| 2014/0142594 A1 | 5/2014 | Fojtik |
| 2016/0029920 A1 | 2/2016 | Kronström et al. |

FOREIGN PATENT DOCUMENTS

| | | |
|---|---|---|
| JP | 2005224266 A | 8/2005 |
| JP | 2007520253 A | 7/2007 |

OTHER PUBLICATIONS

European Patent Office, "Extended European Search Report," European Application No. 18748637.8, dated Nov. 6, 2020.

Japan Patent Office, "Reasons for Rejection," Japanese Application No. 2019-542612, dated Aug. 25, 2020.

Japan Patent Office, "Final Notification for Reasons of Rejection," Japanese Application No. 2019-542612, dated May 19, 2021.

* cited by examiner

TISSUE PIERCING ASSEMBLIES

CROSS-REFERENCE TO RELATED APPLICATION

A claim for the benefit of priority to the Feb. 6, 2017 filing date of U.S. Provisional Patent Application No. 62/455,588, titled TISSUE PIERCING ASSEMBLIES WITH LONG STYLETS ("the '588 Provisional Application") is hereby made pursuant to 35 U.S.C. § 119(e). The entire disclosure of the '588 Provisional Application is hereby incorporated herein.

TECHNICAL FIELD

This disclosure relates generally to cannula-stylet assemblies for piercing tissues of a subject's body and, more specifically, to cannula-stylet assemblies with stylets that have lengths that enable introduction of the stylet through an entire length of an assembly including the cannula and a gripping device for manipulating the cannula. This disclosure also relates to medical piercing systems that include gripping devices and cannula-stylet assemblies.

RELATED ART

Cannula-stylet assemblies are often used to access desired locations within a subject's body. When a cannula is provided with a stylet, the length of the stylet slightly exceeds the length of the cannula, which may enable a distal end of the stylet to protrude slightly beyond a distal end of the cannula and/or a proximal end of the stylet to be coupled to a proximal end of the cannula.

In use, an assembly including a cannula and a stylet within a lumen of the cannula may be secured to a distal end of a gripping device, which enables manipulation of the cannula-stylet assembly. The gripping device may be used to force the cannula-stylet assembly through a desired location of a subject's body and manipulated until a distal end of the cannula is believed to have reached a target location within the subject's body. Once the distal end of the cannula is believed to have reached the target location, the gripping device is uncoupled from the cannula-stylet assembly, and the stylet may be uncoupled from and removed from the cannula to enable a healthcare provider to verify whether or not the distal end of the cannula has reached the target location.

If the distal end of the cannula is present at the target location, one or more other medical devices may be used with the cannula to perform an intended medical procedure at or through the target location. If the distal end of the cannula is not present at the target location, the stylet must be reintroduced into the lumen of the cannula and recoupled to the cannula, the cannula-stylet assembly may be recoupled to the distal end of the gripping device, and the cannula must be manipulated further in an effort to position the distal end of the cannula at the target location within the subject's body. The number of steps required to disassemble and reassemble the cannula, the stylet, and optionally the gripping device may be undesirable, and may increase the risk of complications (e.g., that a subject will become infected, etc.) during a tissue piercing procedure, as well as the risk of contamination of any samples that may be obtained through the cannula.

DISCLOSURE

In one aspect, this disclosure relates to a cannula-stylet assembly. A cannula-stylet assembly according to this disclosure includes a cannula and a stylet. In such an assembly, a distal portion of the stylet resides within and substantially fills a lumen of the cannula. A distal end of the stylet may be flush with a distal end of the cannula, or it may protrude slightly beyond the distal end of the cannula.

The cannula of the cannula-stylet assembly has a first length. The stylet of the cannula-stylet assembly has a second length. The stylet is longer than the cannula; thus, the second length exceeds the first length. The extent to which the second length exceeds the first length is about the same as a length of a gripping device to which the cannula is coupled to facilitate manipulation of the cannula in a desired manner. Stated another way, the second length may be about the same as or slightly longer than a length an assembly of the cannula and the gripping device.

A distal end of the cannula may have any suitable shape. As an example, the distal end of the cannula may be tapered. Tapering of the distal end of the cannula may impart it with a beveled or chisel shape. Alternatively, tapering of the distal end of the cannula may impart it with a somewhat pointed shape. A distal end of the stylet may also be tapered to a bevel or a point.

A proximal end of the cannula may be capable of being coupled to a distal end of a gripping device. A proximal end of the stylet may be capable of being coupled to a proximal end of the gripping device.

In another aspect, a medical piercing system is disclosed. Such a system includes a cannula, a stylet, and a gripping device. In some embodiments, the stylet may be significantly longer than the cannula. In other embodiments, the cannula and stylet may have a conventional configuration, in which the stylet is only slightly longer than the cannula.

The gripping device may include any device suitable for manipulating a cannula, including without limitation, the hand-held, manually operable spinning devices, or rooters, disclosed by U.S. patent application Ser. No. 15/890,223, filed on Feb. 6, 2018; Ser. No. 14/076,170, filed on Nov. 8, 2013; No. 61/723,781, filed on Nov. 8, 2012; Ser. No. 13/039,831, filed on Mar. 3, 2011; and Ser. No. 12/907,926, filed on Oct. 19, 2010, the entire disclosures of which are hereby incorporated herein. Such a rooter may be capable of being held and operated by a single hand of an individual. With a cannula-stylet assembly according to this disclosure is used with a hand-held, manually operable rooter, the rooter may rotate one or both of the cannula and the stylet (i.e., the cannula may rotate while the stylet does not, the stylet may rotate while the cannula does not, the cannula and the stylet may rotate together).

In embodiments where the stylet is significantly longer than the cannula, and where the length of the stylet enables it to extend through the length of the cannula and through the length of a gripping device that has been coupled to a proximal end of the cannula, the stylet may be coupled to the proximal side of the gripping device. In such embodiments, the gripping device may remain coupled to the cannula while the stylet is removed from the cannula. Thus, some of the steps that are required by conventional tissue piercing processes are eliminated, thereby lowering the risk of complications, such as infection, to the subject whose tissue is being pierced, as well as the risk of contaminating of any samples that may be obtained through the cannula. If further manipulation of the cannula is required or desired, the stylet may simply be replaced through the gripping device and within the cannula, and then secured in place to the gripping device to reassemble the medical piercing system.

A method for using such a manual piercing system to pierce and, optionally, collect samples of a subject's tissue(s) includes securing a cannula to a distal end of a gripping device; introducing a stylet that is significantly longer than the cannula into a proximal end of the gripping device, through the gripping device, and into and through a lumen of the cannula; and securing the stylet to the proximal end of a drive feature of the gripping device (e.g., to a proximal end of a drive shaft of a hand-held, manually operable rooter, etc.). The distal end of the cannula may then be positioned on a desired location of the subject's body, and the gripping device manipulated to force the cannula into the subject's body at the desired location and to force a distal end of the cannula toward a target location. Once the distal end of the cannula is believed to have reached the target location, the stylet may be removed from the gripping device and from the cannula to enable determination of a location of the distal end of the cannula within the subject's body (e.g., with a sampling device, etc.). The proximal end of the cannula may remain coupled to the distal end of the gripping device during and after removal of the stylet from the cannula and the gripping device. If further positioning of the distal end of the cannula is desired or necessary, the stylet may be reintroduced into the gripping device and the cannula and secured to the gripping, the position of the cannula may then be adjusted, and the location of the distal end of the cannula may again be determined.

In other embodiments, a manual piercing system may include a gripping device and a conventionally configured cannula-stylet assembly, in which the cannula and stylet have conventional lengths (e.g., in which the stylet is only slightly longer than the cannula, etc.). A coupling component at a proximal end of the stylet may be capable of engaging a coupling component at a distal end of the gripping device. In a specific, but non-limiting embodiment, the coupling component may include a socket or other female feature that can receive a complementarily shaped distal portion, or male feature, at the distal end of the gripping device. Such a manual piercing system may also eliminate some of the steps that are required by conventional tissue piercing processes, thereby lowering the risk of complications, such as infection, to the subject whose tissue is being pierced, as well as the risk of contaminating of any samples that may be obtained through the cannula. If further manipulation of the cannula is required or desired, while the stylet remains coupled to the gripping element, the stylet may simply be replaced within the cannula and secured to the cannula to reassemble the medical piercing system.

A method for using such a manual piercing system that includes a conventionally configured cannula-stylet assembly to pierce and, optionally, collect samples of a subject's tissue(s) includes securing the stylet of a cannula-stylet assembly to a distal end of a gripping device. The distal end of the cannula may then be positioned on a desired location of the subject's body, and the gripping device manipulated to force the cannula into the subject's body at the desired location and to force a distal end of the cannula toward a target location. Once the distal end of the cannula is believed to have reached the target location, the stylet, while remaining coupled to the gripping device, may be removed from the cannula and a sampling device may optionally be used to enable determination of a location of the distal end of the cannula within the subject's body. If further positioning of the distal end of the cannula is desired or necessary, the stylet may be reintroduced into and secured to the cannula, which simultaneously secures the gripping device to the cannula, the position of the cannula may then be adjusted, and the location of the distal end of the cannula may again be determined.

If removing the stylet enables a healthcare professional to determine that the distal end of the cannula has been advanced to the target location, a sampling device coupled to a proximal end of the gripping device (e.g., to a feature to which the proximal end of the stylet was coupled, etc.) may be used to obtain additional material (e.g., a sample, etc.). If, in the alternative, removal of the stylet reveals that the distal end of the cannula has not been advanced to the target location, the stylet may be repositioning in the gripping device and in the lumen of the cannula and the proximal end of the stylet may be re-secured to the proximal end of the gripping device. The gripping device may then be further manipulated to further advance the cannula into the subject's body or to reposition the cannula within the subject's body. Thereafter, the stylet may once again be removed from the cannula and the gripping device to enable a determination of whether or not the distal end of the cannula is present at the target location.

Other aspects, as well as features and advantages of various aspects of the disclosed subject matter will become apparent to those of ordinary skill in the art through consideration of the ensuing description, the accompanying drawings, and the appended claims.

DETAILED DESCRIPTION

Figure 1:
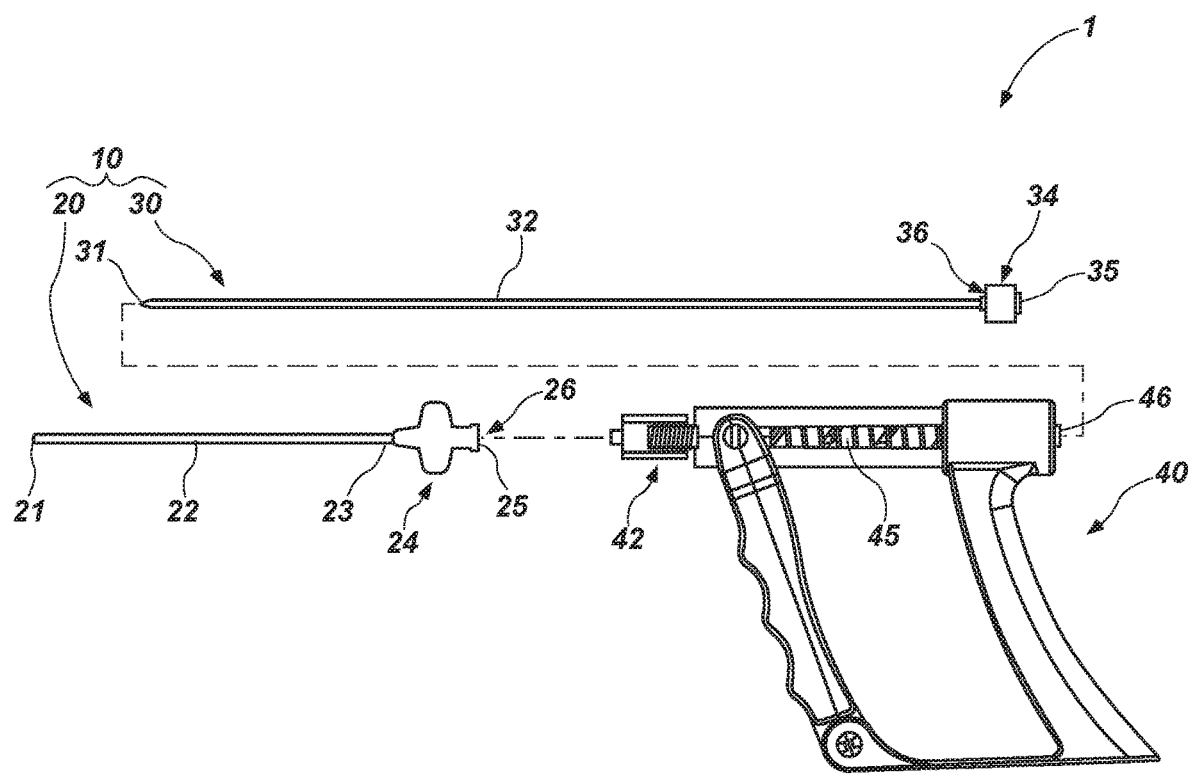
FIG. 1 is an exploded view showing an embodiment of a cannula-stylet assembly with a long stylet, as well as a medical piercing system that includes the cannula-stylet assembly and a gripping device.

With reference to FIG. 1, an embodiment of a cannula-stylet assembly 10 is depicted. Cannula-stylet assembly 10 includes a cannula 20 and a stylet 30. Notably, the stylet 30 is significantly longer than the cannula 20. As depicted, the stylet 30 has a length that enables it to extend completely through the cannula 20 and through the length of a gripping device 40 to which the cannula 20 has been coupled.

The cannula 20 includes a piercing element 22 and a hub 24. The piercing element 22 of the cannula 20 may have any suitable configuration and dimensions. As an example, the piercing element 22 of the cannula 20 may be straight and tapered at its distal end 21. Straight, tapered piercing elements 22 that are 15 G (gauge) in diameter and have lengths of 1.5 cm, 2.5 cm, and 4.5 cm may be suitable for intraosseous use. Straight, tapered piercing elements 22 that are 8 G, 10 G, 11 G, and 12 G in diameter and that have lengths of 10 cm may be used to biopsy bone and bone marrow. Straight, tapered piercing elements 22 that are 15 G in diameter and have lengths of 10 cm may be used generally (e.g., for obtaining biopsies from soft tissue, etc.). Straight, tapered piercing elements 22 that are 17 G, 19 G, and 21 G in diameter and have lengths of 10 cm may also be used generally. Straight, tapered piercing elements 22 that have diameters of 15 G, 17 G, and 19 G and lengths of 15 cm may be used generally and for disc decompression in subject's spinal column.

Alternatively, the piercing element 22 of the cannula 20 may be beveled. Beveled cannulas with 13 G, 11 G, and 9 G diameters and lengths of 10 cm may be used generally and to obtain samples from bone.

The hub 24 of the cannula 20 is located on a proximal end 23 of the piercing element 22. The hub 24 may comprise an enlarge component that may be grasped in a manner that facilitates removal of the stylet 30 from a lumen (not shown) that extends through the piercing element 22 of cannula 20. The hub 24 may also be configured to rest against a surface (e.g., a subject's skin, etc.), when the piercing element 22 has been fully inserted into the subject's body S (see, e.g., FIGS. 3-5). At its proximal end 25, the hub 24 may include a port 26 that communicates with the lumen that extends through the piercing element 22 of the cannula 20 to enable introduction of a stylet into the lumen. The port 26 may be configured to receive and couple with a distal coupling component 42 of a gripping device 40 (e.g., adjacent to or on a distal end of a drive shaft 45 of the gripping device 40, etc.). In some embodiments, the port 26 may be configured as a socket that is shaped complementarily to the gripping device 40 to facilitate spinning of the cannula 20 and its piercing element 22 (e.g., hexagonally, as a square, with a TORX configuration, etc.).

The stylet 30 includes a distal tip 31 at the distal end of a piercing element 32, as well as a hub 34 at the proximal end of the piercing element 32. The distal tip 31 may include a bevel. The bevel may have three or more sides to facilitate introduction of the piercing element 32 and the piercing element 22 of a cannula 20 with which the stylet 30 is assembled into tissue of a subject's body, particularly when the piercing element 32 of the stylet 30 (and, optionally, the piercing element 22 of the cannula 20) is (are) rotated about its (their) longitudinal axis (axes).

Figure 2:
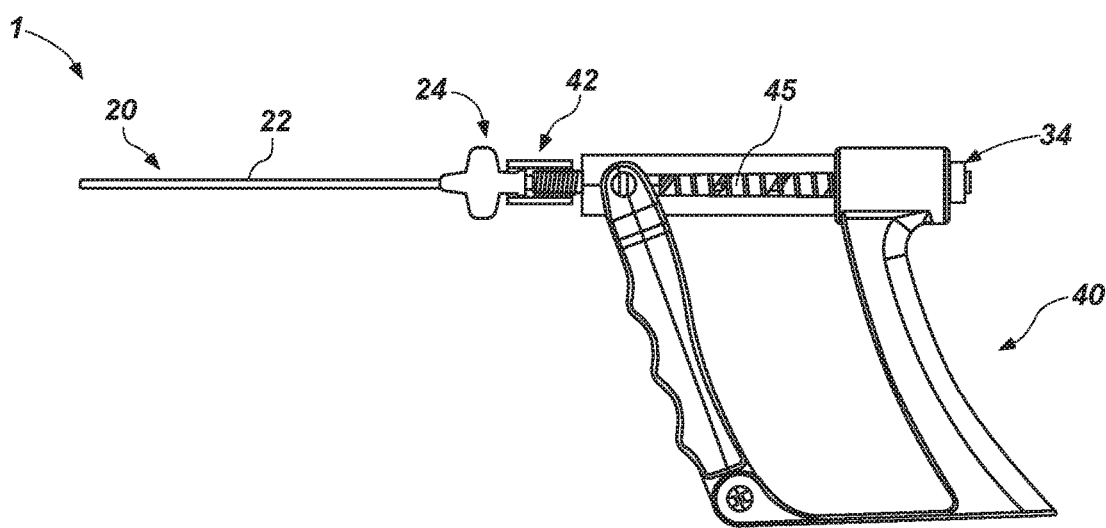
FIG. 2 shows the assembled medical piercing system of FIG. 1, including the cannula-stylet assembly of FIG. 1 assembled with the gripping device of FIG. 1.

The piercing element 32 of the stylet 30 has a length that enables it to extend completely through the lumen of the piercing element 22 of the cannula 20 and completely through a conduit through a gripping device 40 to which the cannula 20 has been coupled. When the cannula 20, the gripping device 40, and the stylet 30 are assembled, as illustrated by FIG. 2, the length of the piercing element 32 of the stylet 30 should enable the distal tip 31 to protrude beyond the distal end 21 of the piercing element 22 of the cannula 20. The distance by which the distal tip 31 of the piercing element 32 of the stylet 30 protrudes beyond the distal end 21 of the piercing element 22 of the cannula 20 may prevent a bevel at the distal tip 31 of the piercing element 32 of the stylet 30 from overlapping, or being located at the same longitudinal position of the cannula-stylet assembly 10, as the distal end 21 of the piercing element 22 of the cannula 20.

The hub 34 of the stylet 30 includes a distally facing coupling feature 36 that enables the stylet 30 to be coupled to a proximal coupling component 46 of the gripping device 40 (e.g., on a proximal end of the drive shaft 45 of the gripping device 40, etc.). The distally facing coupling feature 36 of the hub 34 of the stylet 30 may comprise a female threaded element (e.g., a female luer cap, etc.) that receives a complementarily threaded male element of the proximal coupling component 46 of the gripping device 40.

The gripping device 40 may comprise any device suitable for manipulating the cannula 20 and the stylet 30. In the depicted embodiment, the gripping device 40 includes a hand-held, manually operable spinning device. A drive shaft 45 of the gripping device 40 may be driven, or rotated, in a manner that rotates the proximal coupling component 46 and that may optionally rotate the distal coupling component 42. A conduit (not shown) that extends through the proximal coupling component 46, the drive shaft 45, and the distal coupling component 42 may accommodate a portion of the piercing element 32 of the stylet 30, enabling the piercing element 32 of the stylet 30 to extend through the gripping device 40.

Figure 3:
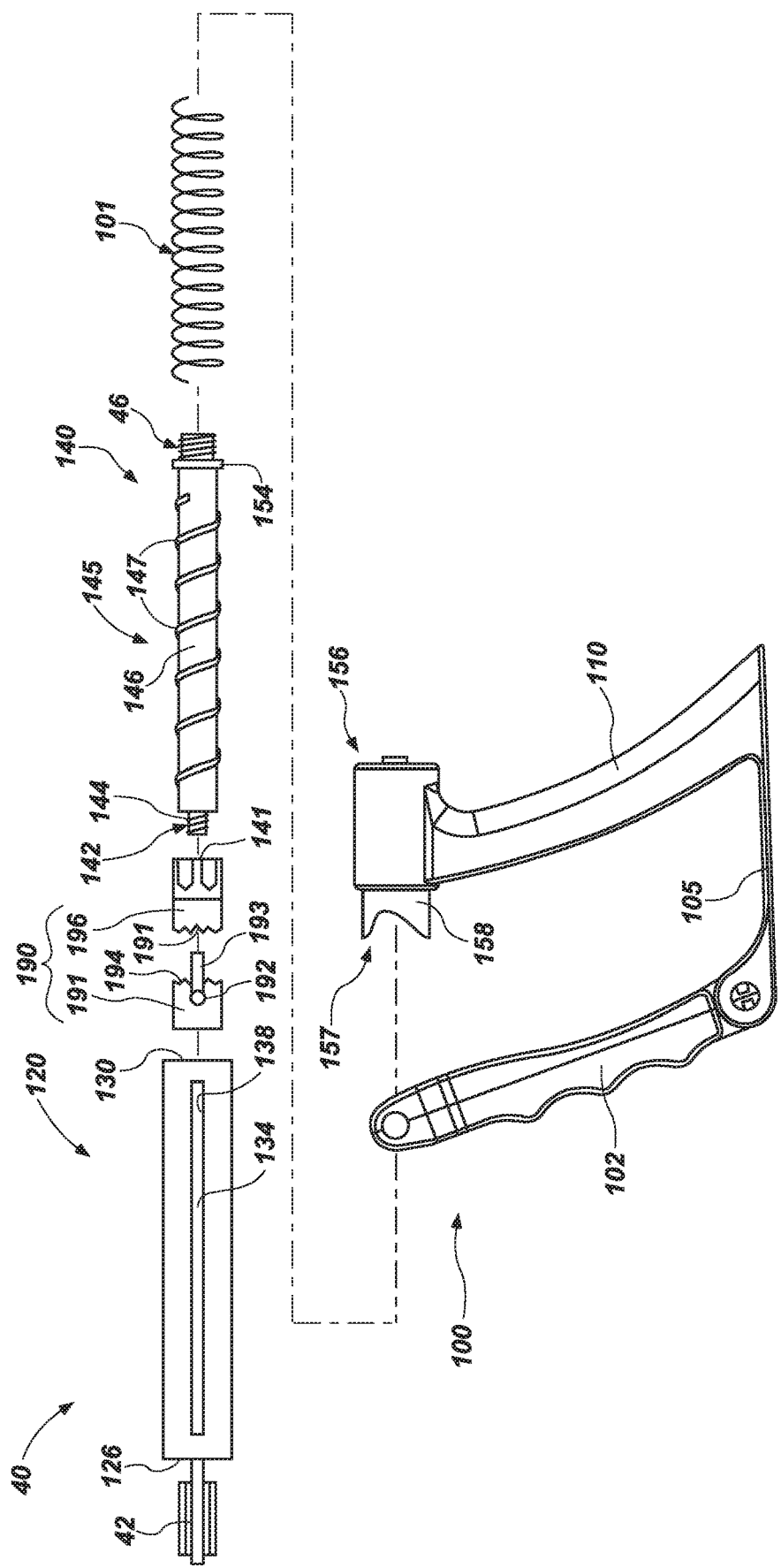
FIG. 3 provides an exploded view of a specific embodiment of gripping device that may be included in a medical piercing system.

A specific embodiment of gripping device 40 that may be included in a medical piercing system 1 according to this disclosure is depicted by FIG. 3. The gripping device 40 includes a drive shaft 140 that comprises an elongated element configured to be assembled with a housing 120 of the gripping device 40. The drive shaft 140 may be tubular and, thus, include a conduit 55 extending through its entire length. A longitudinal axis 141 of the drive shaft 140 extends centrally or substantially centrally through a length of the drive shaft 140. The conduit 155 and the longitudinal axis 141 of the drive shaft 140 may be aligned (e.g., concentric, etc.).

The drive shaft 140 includes an intermediate portion 145, as well as a distal portion 142 and a proximal portion 150 at opposite ends of the intermediate portion 145. The intermediate portion 145, which may be generally cylindrical in shape, includes a rotation facilitator 147. In the illustrated embodiment, the rotation facilitator 147 comprises a helical ridge, which protrudes from an outer surface 146 of the intermediate portion 145. In particular, the helical ridge 147 may wrap circumferentially around the intermediate portion 145. The helical ridge 147 may be continuous, as illustrated, or it may comprise a discontinuous structure. The helical ridge 147 extends along at least a portion of the length of the intermediate portion 145. In some embodiments, the helical ridge 147 may extend along only a part of the intermediate portion 145, as in the depicted embodiment, where the ends of the helical ridge 147 are spaced apart from corresponding ends of the intermediate portion 145.

The distal portion 142 of the drive shaft 140 may also be cylindrical in shape. The distal portion 142 of the drive shaft 140 may have a smaller diameter than the intermediate portion 145 of the drive shaft 140. Thus, a circumferential ledge 144 may be present at the boundary between the distal portion 142 and the intermediate portion 145. The distal portion 142 may also be configured to pass through an opening (not shown) in the distal end 126 of the housing 120, and to protrude from the distal end 126. The distal portion 142 may be configured to engage or be engaged by the distal coupling component 42. In this regard, a distal portion 142 of some embodiments of a drive shaft 140 of a gripping device 40 may include one or more retention features, such as the helical thread shown in FIG. 3.

The proximal portion 150 of the drive shaft 140 may likewise have a cylindrical shape. In some embodiments, the proximal portion 150 may be configured to protrude beyond the proximal end 130 of the housing 120 of the gripping device 40. The proximal portion 150 of the drive shaft 140 may at least partially define the proximal coupling component 46 of the gripping device 40.

A circumferential rim 154, which extends around and protrudes from the outer surface 146 of the drive shaft 140, may delimit, or define a boundary between, the intermediate portion 145 of the drive shaft 140 and its proximal portion 150. The circumferential rim 154 may provide a stop for a proximal member 196 of an actuator 190 that cooperates with the drive shaft 140.

The actuator 190 may comprise ratcheting actuator, which enables the drive shaft 140 of the gripping device 40 to continuously drive in a forward direction, even if resistance of a device coupled to the distal coupling component 42 prevents rotation of the drive shaft 140 in a reverse direction. Such an actuator 190 may include a distal member 191 and the proximal member 196. The distal member 191 comprises a cylindrical element with an aperture extending through its length. The aperture is configured to receive the drive shaft 140 and, more specifically, to receive the intermediate portion 145 of the drive shaft 140 in a manner that enables the cylindrical element of the distal member 191 to slide, or move, along the length of the drive shaft 140, without engaging the rotation facilitator 147 of the drive shaft 140.

The distal member 191 of the actuator 190 includes a pair of intermediate elements (not shown) protruding from opposite sides of the cylindrical element and external elements 192 on the ends of the intermediate elements. The intermediate elements of the distal member 191 are capable of being received by a longitudinal slot 134 through the housing 120 of the gripping device 40. The external elements 192 are capable of protruding from the housing 120 and being received by and coupling with corresponding features on a moveable element 102 of a handle 100 of the gripping device 40. Thus, the intermediate elements and the external elements 192 of the distal member 191 of the actuator 190 enable movement of the distal member 191 of the actuator 190 along the length of the drive shaft 140.

At its proximal end, the distal member 191 of the actuator 190 includes alignment features 193 and engagement features that comprise teeth 194. The alignment features 193 protrude beyond the proximal end of the distal member 191 and are spaced apart and capable of receiving and aligning (e.g., they may be tapered, etc.) the proximal member 196 of the actuator 190 with the distal member 191. The teeth 194, which are formed in a proximal edge of the distal member 191, are configured to engage corresponding engagement features of the proximal member 196.

Those corresponding engagement features of the proximal member 196 of the actuator 190 comprise teeth 197 formed in a distal edge of the proximal member 196. In addition to the teeth 197, the proximal member 196 includes a cylindrical body, an aperture (not shown) extending through the cylindrical body, and one or more drive features (not shown) formed in the surface of the aperture. The drive features may be capable of engaging a corresponding rotation facilitator 147 of the intermediate portion 145 of the drive shaft 140. More specifically, the drive features may receive and engage the helical ridge 147 of the intermediate portion 145 of the drive shaft 140.

The teeth 197 of the proximal member 196 and the teeth 194 of the distal member 191 may be configured in such a way that the teeth 194 of the distal member 191 will engage the teeth 197 of the proximal member 196 as the distal member 191 is forced proximally, causing the rotatable element 145 to rotate in a first direction, or in a forward direction (e.g., clockwise), but enable the teeth 194 of the distal member 191 to disengage the teeth 197 of the proximal member 196 as the proximal member 196 is forced distally (e.g., by a return element 101, etc.) and rotates in an opposite, second direction, or in a reverse direction (e.g., counterclockwise), such as when resistance on a cannula 20 and/or stylet 30 that has been coupled to the rotatable element 145 resists rotation in the second direction. In the illustrated embodiment, each tooth 194, 197 may include a radially oriented drive surface and a somewhat circumferentially oriented slip surface that tapers outward from the base of one drive surface to the top of the next drive surface.

The gripping device 40 may also include a return element 101, which is also referred to herein as a "biasing element," (e.g., a spring, etc.) that causes the actuator 190 and the moveable element 102 of the handle 100 to return to or substantially return to an initial position. When the moveable element 102 is moved in a first direction (e.g., proximally, etc.), energy may be stored in the return element 101. When the moveable element 102 is released, the resilience of the return element 101, and the energy stored within the return element 101, may cause the actuator 190 and the moveable element 102 of the handle 100 to move in an opposite, second direction (e.g., distally, etc.) along the lengths of the housing 120 and the drive shaft 140 of the gripping device 40. The return element 101 may comprise an internal compression spring, which may concentrically surround the drive shaft 140 of the gripping device 40 is capable of being compressed between a proximal edge of the cylindrical element of the proximal member 196 of the actuator 190 and an interior surface of the end 158 of a cap 156 at a proximal end of the drive shaft 140 as the moveable element 102 and, thus, the cylindrical element of the proximal member 196 of the actuator 190 are force proximally along the drive shaft 140 and the housing 120. A distal end of the return element 101 abuts the proximal edge of the cylindrical element of the proximal member 196 of the actuator 190, while a proximal end of the return element 101 is held in place against the interior surface of the end 158 of the cap 156.

A return element that is centered around the drive shaft 140, such as the compression spring embodiments of the return element 101 shown in FIG. 3, may enable the cylindrical element of the proximal member 196 of the actuator 190 to remain concentric or substantially concentric with the axis 141 of the drive shaft 140. Thus, such a return element may prevent cocking of the actuator 190 relative to the drive shaft 140 and may facilitate smooth strokes as the actuator 190 moves along the length of the drive shaft 140. Of course, other embodiments of return elements 101, including other types of internal springs, external springs (e.g., a torsion spring, which may be positioned between the moveable element 102 and the elongated handle 110 or equivalent features, etc.), and other apparatuses that will cause the actuator 190 to automatically reverse its position may be included in a gripping device 40.

The automatic return of the actuator 190 to its initial position may also cause the drive shaft 140 to rotate in its opposite direction, provided that any rotational resistance on a device (e.g., a cannula 20, a stylet, etc.) that has been coupled to the distal coupling component 42 is not sufficient to overcome the biasing force of the return element 101. In the event that rotational resistance on the device is sufficient to overcome the biasing force of the return element 101, the proximal member 196 of the actuator 190 may disengage the distal member 191 of the actuator 190, enabling the distal member 191 to slide distally along the drive shaft 140 and the proximal member 196 to rotate freely relative to the drive shaft 140, enabling the proximal member 196 to move distally along the length of the drive shaft 140 and to force the distal member 191 distally along the length of the drive shaft 140.

Rotation of a device (e.g., about its longitudinal axis, etc.) may occur by causing the drive shaft 140, as well as the distal coupling component 42 and/or the proximal coupling component 46 to rotate (e.g., about longitudinal axis 141 of the drive shaft 140, etc.). In the illustrated embodiment, such rotation may be caused by moving the moveable element 102 of the handle 100 of the gripping device 40 along the length of the gripping device 40's housing 120. As the moveable element 102 is moved along the length of the housing 120, the intermediate element (not shown) of the distal member 191 of the actuator 190 moves through the longitudinal slot 134 in the housing 120, which causes the cylindrical element of the distal member 191 of the actuator 190 within the interior 124 of the housing 120 to move along the length of the drive shaft 140. As the cylindrical element of the distal member 191 of the actuator 190 moves proximally along the length of the drive shaft 140, it forces the cylindrical element of the proximal member 196 of the actuator 190 to move proximally along the length of the drive shaft 140. As the cylindrical element of the proximal member 196 of the actuator 190 moves proximally, drive features (not shown) on or in the interior surface of the aperture (not shown) of the cylindrical element of the proximal member 196 may engage the complementarily configured rotation facilitator 147 of the drive shaft 140 (e.g., the depicted helical ridge, etc.). The configurations of the longitudinal slot 134 and the actuator 190 (specifically, the intermediate element(s) of the distal member 191 of the actuator 190) may prevent rotation of the cylindrical element of the distal member 191 within an interior of the housing 120, or at least enable the drive shaft 140 to rotate relative to the housing 120. During rotation of the drive shaft 140, one or both of the distal coupling component 42 and the proximal coupling component 46 may also rotate relative to the housing 120, which rotation may also cause the device that is to be rotated to spin relative to the housing 120 of the gripping device 40. If the gripping device 40 is held stationary, or at least substantially stationary, movement of the moveable element 102 of the handle 100 may cause the device to rotate or spin.

Upon releasing the movable element 102 of the handle 100 of the gripping device 40, the return element 101 may force the proximal member 196 and the distal member 191 of the actuator 190 in a distal direction along the length of the drive shaft 140. If the force the return element 101 exerts on the proximal member 196 exceeds a rotational resistance on a device that has been coupled to the distal coupling component 42 (and, thus, to the drive shaft 140), the proximal member 196 of the actuator 190 may remain rotationally stationary over the drive shaft 140, distal movement of the proximal member 196 of the actuator 190 may drive the drive shaft 140 and the rotated device in a reverse direction, thus enabling oscillation of the drive shaft 140 and of the rotated device. If the rotational resistance on the rotated device exceeds the biasing force the biasing member exerts on the proximal member 196 of the actuator 190, the teeth 197 of the proximal member 196 may disengage their corresponding teeth 194 on the distal member 191 of the actuator 190, enabling the proximal member 196 to rotate over the drive shaft 140 and, thus, enabling the return element 101 to force the proximal member 196 distally along the drive shaft 140 with limited rotation or no rotation of the drive shaft 140 (i.e., the proximal member 196, rather than the drive shaft 140, may spin when the proximal member 196 moves distally), forcing the distal member 191 of the actuator 190 distally over the drive shaft 140 and forcing the moveable member 102 of the handle 100 distally as well.

Figure 4:
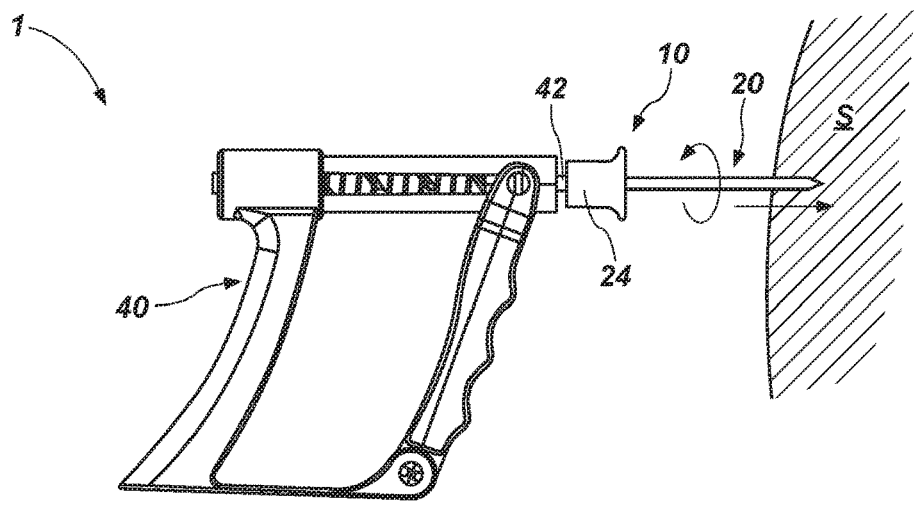
FIGS. 4-6 illustrate use of the cannula-stylet assembly of FIGS. 1 and 2.
Figure 5:
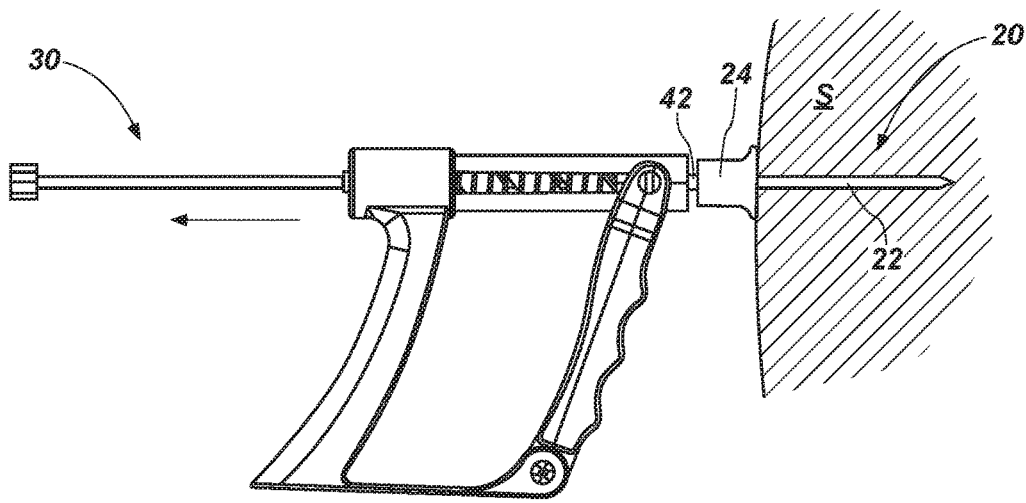
Figure 6:
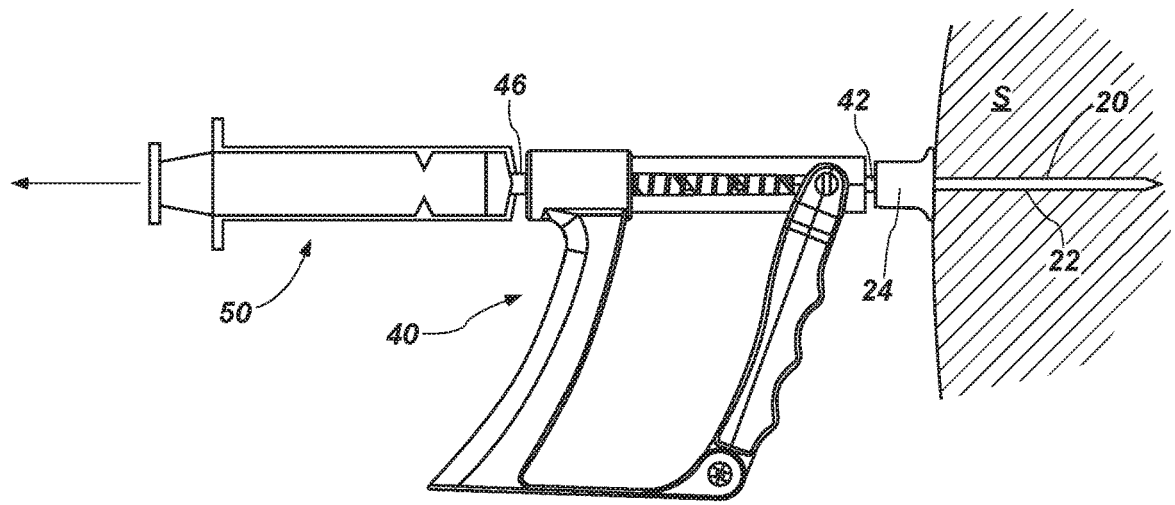

Looking again to FIG. 2, when the cannula 20 and the stylet 30 are assembled with a gripping device 40, the resulting medical piercing system 1 may be used in a variety of procedures to obtain samples or remove materials from the body of a subject S. FIGS. 4-6 illustrate the manner in which such a medical piercing system 1 may be used.

As illustrated by FIG. 4, the piercing element 22 of the cannula 20 of the medical piercing system 1, as well as the distal tip 31 (FIG. 1) of the piercing element 32 (FIG. 1) of the stylet 30 may be forced into tissue of a subject S. Introduction of the piercing elements 22 and 32 into the tissue may be conducted by applying pressure to the gripping device 40 distally, in a direction toward a site of interest in the body of the subject S. In some embodiments, such force may be accompanied by rotating one or both of the piercing elements 22 and 32 with the gripping device 40, which may further facilitate introduction of the piercing elements 22 and 32 into the body of the subject S (e.g., reduce the force required to introduce the piercing elements 22 and 32, speed up the process of introducing the piercing elements 22 and 32, etc.).

Once the distal end 21 of the piercing element 22 of the cannula 20 is believed to be at a desired location within the body of the subject S, the stylet 30 may be disassembled from the gripping device 40 and from the cannula 20, as depicted by FIG. 5. More specifically, the coupling feature 36 (FIG. 1) of the hub 34 of the stylet 30 may be uncoupled from the proximal coupling component 46 of the gripping device 40, and the piercing element 32 of the stylet 30 may be pulled out of the lumen of the piercing element 22 of the cannula 20 and out of the conduit that extends through the distal coupling component 42, the drive shaft 45, and the proximal coupling component 46 of the gripping device 40.

Next, as FIG. 6 shows, a syringe or another aspiration device 50 may be coupled to the proximal coupling element 46 of the gripping device 40, and used to aspirate material (e.g., a sample, etc.) through the piercing element 22 of the cannula 20 and through the conduit that extends through the distal coupling component 42, the drive shaft 45, and the proximal coupling component 46 of the gripping device 40. If an expected material is withdrawn by the aspiration device 50, withdrawal of material may continue. If the expected material is not withdrawn, the aspiration device 50 may be removed from the gripping device 40, the stylet 30 (FIG. 5) may be replaced on the gripping device 40, and the processes depicted by FIGS. 4-6 may be repeated.

Figure 7:
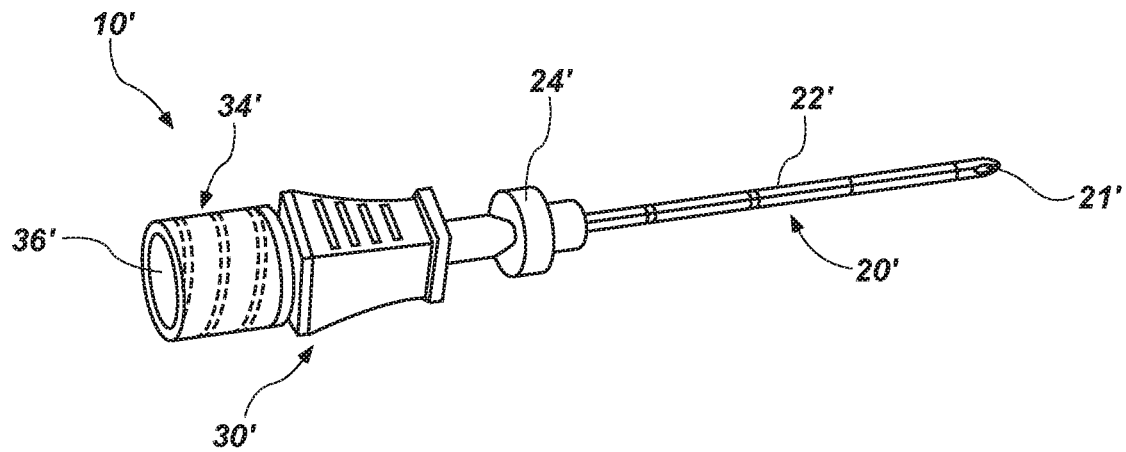
FIG. 7 shows a conventional cannula-stylet assembly.
Figure 8:
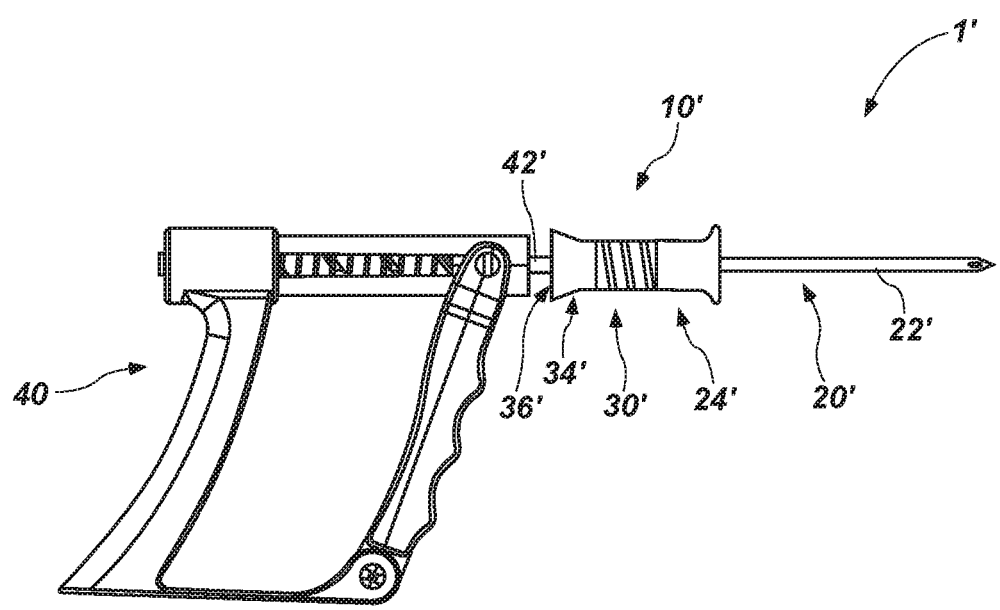
FIG. 8 depicts another embodiment of manual piercing system, which includes a conventional cannula-stylet assembly and a gripping device.

Turning now to FIGS. 7 and 8 a conventionally configured cannula-stylet assembly 10' is depicted. The conventionally configured cannula-stylet assembly 10' includes a cannula 20' and a stylet 30'. The cannula 20' includes a piercing element 22' with a distal end 21' that is capable of being introduced into and through tissues of a subject's body, as well as a hub 24' at a proximal end of the piercing element 22'. The stylet 30' includes a piercing element (not shown) that is only slightly longer than the cannula 20'. In addition, the stylet 30' includes a hub 34' at a proximal end of the piercing element, with a proximally facing coupling feature 36' on a proximal side of the hub 34'.

As illustrated by FIG. 8, the proximally facing coupling feature 36' of the hub 34' of the stylet 30' may be capable of coupling with a distal coupling component 42 of a gripping device 40. The proximally facing coupling feature 36' of the stylet 30' may be configured to mate with (e.g., receive, be received by, etc.) the distal coupling component 42' of the gripping device 40.

In some embodiments, both a long stylet 30 (FIG. 1) and a stylet 30' of conventional length may be packaged with a cannula 20' with a length that corresponds to the length of the stylet 30' of conventional length.

Figure 9:
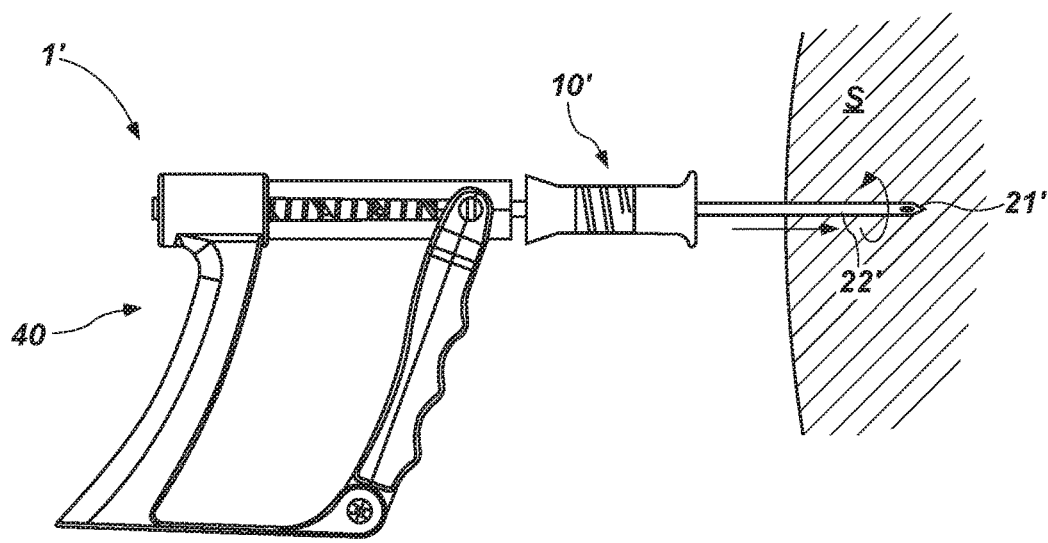
FIGS. 9-11 illustrate use of the cannula-stylet assembly of FIG. 8.
Figure 10:
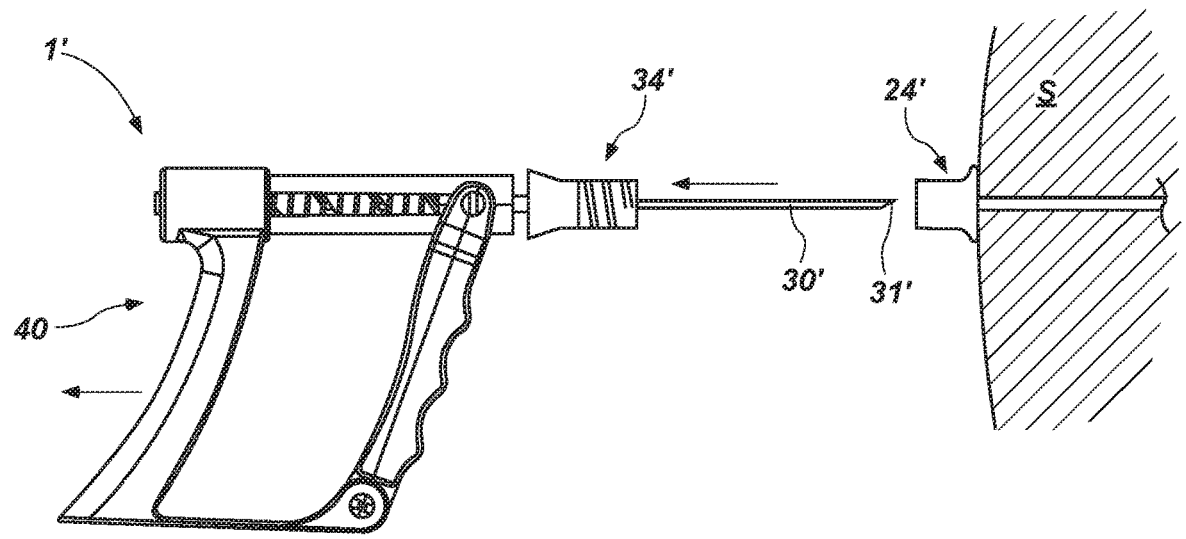
Figure 11:
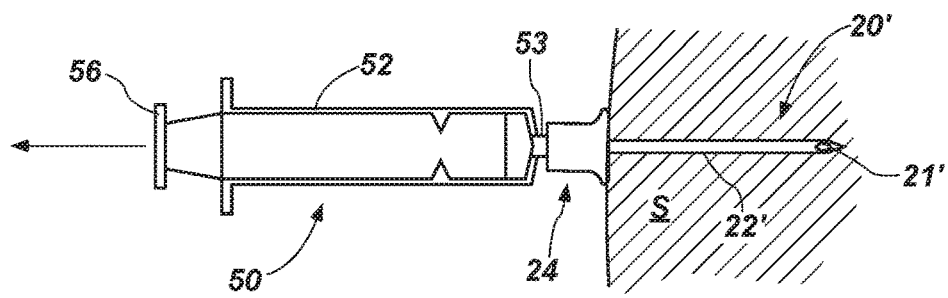

When the cannula 20' and the stylet 30' are assembled with a gripping device 40 in the manner shown in FIG. 8, the resulting medical piercing system 1' may be used in a variety of procedures to obtain samples or remove materials from the body of a subject S. FIGS. 9-11 illustrate the manner in which such a medical piercing system 1' may be used.

As FIG. 9 shows, with the hubs 24' and 34' coupling the cannula 20' and the stylet 30' to one another, the piercing element 22' of the cannula 20' of the medical piercing system 1', as well as the distal tip 31' (FIG. 7) of the piercing element 32' (FIG. 7) of the stylet 30' may be forced into tissue of a subject S. Introduction of the piercing elements 22' and 32' into the tissue may be conducted by applying pressure to the gripping device 40 distally, in a direction toward a site of interest in the body of the subject S. In some embodiments, such force may be accompanied by rotating the piercing elements 22' and 32' with the gripping device 40, which may further facilitate introduction of the piercing elements 22' and '32 into the body of the subject S (e.g., reduce the force required to introduce the piercing elements 22' and 32', speed up the process of introducing the piercing elements 22' and 32', etc.).

Once the distal end 21' of the piercing element 22' of the cannula 20' is believed to be at a desired location within the body of the subject S, the stylet 30' may be disassembled from the cannula 20', as depicted by FIG. 10. More specifically, while the hub 34' of the stylet 30' remains secured to the distal coupling component 42 of the gripping device 40, the hub 34' of the stylet 30' may be uncoupled from the hub 24' of the cannula 20', and the piercing element 32' of the stylet 30' may be pulled out of the lumen of the piercing element 22' of the cannula 20'.

Next, as FIG. 11 shows, a syringe or another aspiration device 50 may be coupled to the hub 24' of the cannula 20', and used to aspirate material (e.g., a sample, etc.) through the piercing element 22' of the cannula 20'. If an expected material is withdrawn by the aspiration device 50, withdrawal of material may continue. If the expected material is not withdrawn, the aspiration device 50 may be removed from the hub 24' of the cannula 20, and the stylet 30' (FIG. 10) may again be assembled with the cannula 20'. More specifically, the hub 34' of the stylet 30' may be coupled to the hub 24' of the cannula 20'. Since the stylet 30' remains assembled with the gripping device 40, assembly of the stylet 30' with the cannula 20' also assembles the gripping device 40 with the cannula 20'. The processes depicted by FIGS. 9-11 may then be repeated.

As suggested previously herein, a medical piercing system 1, 1' (FIGS. 2 and 5, respectively) according to this disclosure may be used for a variety of purposes, including biopsies of soft tissue and decompression of intervertebral discs. When a gripping device 40 with a ratcheting actuator 190 (FIG. 3) is used in with a medical piercing system 1, 1' of this disclosure, the actuator 190 may enable a cannula 20, 20' and/or a stylet 30, 30' of the medical piercing system 1, 1' to repeatedly rotate in a single direction (e.g., in a pulsed manner, with each proximal movement of the moveable element 102 (FIG. 3) of the handle 100 (FIG. 3). Such movement of the cannula 20, 20' and/or the stylet 30, 30' may facilitate drill into dense tissues, including bone, which might otherwise resist reversal of the direction in which a cannula 20, 20' and/or a stylet 30, 30' rotates. Use of a medical piercing system 1, 1' that includes the disclosed gripping device 40 may provide a user (e.g., a healthcare professional, etc.) with a feel for the density of the tissue into which the distal tip 31 of the piercing element 32 of the stylet 30 and the distal end 21 of the piercing element 22 of the cannula 20 are introduced. The tactile feedback the user receives may improve the user's ability to adapt to conditions he or she encounters while introducing the piercing element of the cannula 20 into a subject's body and to predict when the distal end 21 of the piercing element 22 of the cannula 20 has reached a desired location within the subject's body.

Although the foregoing description sets forth many specifics, these should not be construed as limiting the scope of any of the claims, but merely as providing illustrations of some embodiments and variations of elements or features of the disclosed subject matter. Other embodiments of the disclosed subject matter may be devised which do not depart from the spirit or scope of any of the claims. Features from different embodiments may be employed in combination. Accordingly, the scope of each claim is limited only by its plain language and the legal equivalents thereto.

What is claimed:

1. A cannula-stylet assembly, comprising:
a cannula having a first length and including a piercing element at a distal end of the cannula and a hub at a proximal end of the cannula that couples to and uncouples from a distal side of a gripping device; and
a stylet including a piercing element at a distal end of the stylet and a hub at a proximal end of the stylet, the piercing element of the stylet insertable into the gripping device, the hub of the stylet securable to a proximal side of the gripping device, the stylet having a second length, the second length being at least as long as a combined length of an assembly including the cannula and the gripping device,
the hub of the cannula and the hub of the stylet having configurations that enable one of the cannula and the stylet to rotate while another of the cannula and the stylet remains rotationally stationary relative to the gripping device.

2. The cannula-stylet assembly of claim 1, wherein the second length is at least as long as a length of an assembly including the cannula and a rooter to which the cannula is coupled.

3. The cannula-stylet assembly of claim 1, wherein the distal end of the cannula is tapered.

4. The cannula-stylet assembly of claim 1, wherein the distal end of the cannula is beveled.

5. The cannula-stylet assembly of claim 1, wherein the hub of the stylet is located at a proximal end of the stylet and couples the stylet to a proximal coupling component on the proximal side of the gripping device.

6. A medical piercing system, comprising:
a gripping device comprising a hand-held, manually operable rooter with a drive shaft rotatable relative to a remainder of the hand-held, manually operable rooter and having an axis of rotation extending through a length of the drive shaft;
a cannula; and
a stylet,
one of the cannula and the stylet coupled to the drive shaft of the hand-held, manually operable rooter to rotate the one of the cannula or the stylet while another of the cannula and the stylet remains rotationally stationary relative to the gripping device.

7. The medical piercing system of claim 6, wherein the stylet extends through a length of the drive shaft of the hand-held, manually operable rooter and through an entire length of a lumen of the cannula, the cannula coupled to a distal end of the hand-held, manually operable rooter, the stylet coupled to a proximal end of the hand-held, manually operable rooter.

8. The medical piercing system of claim 7, wherein the cannula is coupled to a distal end of the drive shaft of the hand-held, manually operable rooter in a manner that enables rotation of the cannula during operation of the hand-held, manually operable rooter.

9. The medical piercing system of claim 7, wherein the stylet is coupled to a proximal end of the drive shaft of the hand-held, manually operable rooter in a manner that enables rotation of the stylet during operation of the hand-held, manually operable rooter.

10. The medical piercing system of claim 9, wherein:
the cannula is coupled to the distal end of the hand-held, manually operable rooter in a manner that enables it to remain rotationally stationary relative to the hand-held, manually operable rooter as the drive shaft of the hand-held, manually operable rooter rotates; and
the stylet is capable of rotating within the lumen of the cannula as the drive shaft of the hand-held, manually operable rooter rotates.

11. The medical piercing system of claim 7, wherein the stylet is removable from the lumen of the cannula and the drive shaft of the hand-held, manually operable rooter while the hand-held, manually operable rooter is coupled to the cannula.

12. The medical piercing system of claim 6, wherein:
the drive shaft extends through a length of the hand-held, manually operable rooter;
the stylet includes a includes a stylet hub that couples to a proximal side of the drive shaft; and
the cannula includes a cannula hub that couples to a distal side of the drive shaft.

13. The medical piercing system of claim 6, wherein:
the stylet includes a stylet hub with a proximal side that couples to a distal side of the drive shaft of the hand-held, manually operable rooter; and
the cannula includes a cannula hub that couples to a distal side of the stylet hub.

14. The medical piercing system of claim 13, wherein the stylet hub includes a female coupler that receives a complementary shaped male coupler on a distal end of the drive shaft.

15. A medical piercing system, comprising:
a gripping device comprising a hand-held, manually operable rooter including a drive shaft extending along a length of the hand-held, manually operable rooter and a conduit extending through a length of the drive shaft, the drive shaft rotatable relative to a remainder of the hand-held, manually operable rooter and having an axis of rotation extending through the length of the drive shaft;
a cannula with a cannula hub at a proximal end of the cannula that couples to and uncouples from a distal side of the hand-held, manually operable rooter; and
a stylet with a stylet hub at a proximal end of the stylet that couples to and uncouples from a proximal side of the hand-held, manually operable rooter,
the cannula hub, the gripping device, and the stylet hub having configurations that enable one of the cannula and the stylet to rotate while another of the cannula and the stylet remains rotationally stationary relative to the gripping device.

16. The medical piercing system of claim 15, wherein the stylet extends through the length of the drive shaft and through an entire length of a lumen of the cannula.

17. The medical piercing system of claim 15, wherein the cannula hub is coupled to a distal side of the drive shaft of the hand-held, manually operable rooter in a manner causes the cannula to rotate during operation of the hand-held, manually operable rooter.

18. The medical piercing system of claim 15, wherein the stylet hub is coupled to a proximal side of the drive shaft of the hand-held, manually operable rooter a manner that causes the stylet to rotate during operation of the hand-held, manually operable rooter.

19. The medical piercing system of claim 18, wherein:
the cannula hub is coupled to the distal side of the hand-held, manually operable rooter in a manner that causes the cannula to remain rotationally stationary relative to the hand-held, manually operable rooter as the drive shaft of the hand-held, manually operable rooter rotates; and
the stylet is capable of rotating within a lumen of the cannula as the drive shaft of the hand-held, manually operable rooter rotates.

20. The medical piercing system of claim 15, wherein the stylet is removable from a lumen of the cannula and the conduit extending through the length of the drive shaft of the hand-held, manually operable rooter while the hand-held, manually operable rooter is coupled to the cannula.

21. A medical piercing system, comprising:
a gripping device comprising a hand-held, manually operable rooter including a drive shaft extending along a length of the hand-held, manually operable rooter;
a stylet with a stylet hub at a proximal end of the stylet, the stylet hub having a proximal side that couples to a distal side of the drive shaft of the hand-held, manually operable rooter; and
a cannula with a cannula hub at a proximal end of the cannula, the cannula hub having a distal side that couples to a proximal side of the stylet hub,
the cannula hub, the gripping device, and the stylet hub having configurations that enable one of the cannula and the stylet to rotate while another of the cannula and the stylet remains rotationally stationary relative to the gripping device.

22. The medical piercing system of claim 21, wherein the proximal side of the stylet hub includes a female coupler that receives a complementary shaped male coupler on a distal end of the drive shaft.

23. The medical piercing system of claim 21, wherein the cannula hub couples to the proximal side of the stylet hub in a manner that enables the cannula to rotate with the stylet and the drive shaft of the hand-held manually operable rooter during operation of the hand-held manually operable rooter.

* * * * *